US010001567B2

(12) United States Patent
Roessl et al.

(10) Patent No.: US 10,001,567 B2
(45) Date of Patent: Jun. 19, 2018

(54) X-RAY DETECTOR, IMAGING APPARATUS AND CALIBRATION METHOD

(71) Applicant: KONINKLIJKE PHILIPS N.V., Eindhoven (NL)

(72) Inventors: Ewald Roessl, Henstedt-Ulzburg (DE); Heiner Daerr, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days. days.

(21) Appl. No.: 15/114,444

(22) PCT Filed: Dec. 9, 2015

(86) PCT No.: PCT/EP2015/079175
§ 371 (c)(1),
(2) Date: Jul. 27, 2016

(87) PCT Pub. No.: WO2016/091981
PCT Pub. Date: Jun. 16, 2016

(65) Prior Publication Data
US 2017/0285186 A1     Oct. 5, 2017

(30) Foreign Application Priority Data
Dec. 11, 2014   (EP) .................................... 14197459

(51) Int. Cl.
*G01T 1/24*     (2006.01)
*A61B 6/00*     (2006.01)
(Continued)

(52) U.S. Cl.
CPC ................ *G01T 1/24* (2013.01); *A61B 6/585* (2013.01); *H05G 1/08* (2013.01); *G01T 7/005* (2013.01); *H01J 35/02* (2013.01)

(58) Field of Classification Search
CPC .. G01T 1/24; G01T 7/005; H05G 1/08; A61B 6/582; A61B 6/585; A61B 6/42; A61B 6/4233
See application file for complete search history.

(56) References Cited

U.S. PATENT DOCUMENTS

2011/0012014 A1*   1/2011   Livne ..................... A61B 6/032
                                                                    378/207
2011/0253886 A1   10/2011   Hackenschmied
2014/0105370 A1*   4/2014   Yamakawa ............ A61B 6/025
                                                                    378/207

FOREIGN PATENT DOCUMENTS

DE   10 2010 015422     10/2011
WO       2014/087290      6/2014

OTHER PUBLICATIONS

Mozzanica, et al., "The COTTHARD charge integrating readout detector: design and characterization", Journal of Instrumentation, Institute of Physics Publishing, vol. 7, No. 1, Jan. 4, 2012.
(Continued)

*Primary Examiner* — Glen Kao
*Assistant Examiner* — Chih-Cheng Kao (57) ABSTRACT

An X-ray detector comprises a directly converting semiconductor layer having a plurality of pixels for converting incident radiation into electrical measurement signals with a band gap energy characteristic of the semiconductor layer, wherein said incident radiation is x-ray radiation emitted by an x-ray source or light omitted by at least one light source. An evaluation unit calculates evaluation signals per pixel or group of pixels from first electrical measurement signals generated when light from said at least one light source at a first intensity is coupled into the semiconductor layer, and second electrical measurement signals generated when light from said at least one light source at a second intensity is coupled into the semiconductor layer. A detection unit
(Continued)

determines detection signals from electrical measurement signals generated when x-ray radiation is incident onto the semiconductor layer, and a calibration unit calibrates the detection unit on the basis of the evaluation signals.

15 Claims, 5 Drawing Sheets (51) Int. Cl.
*H05G 1/08* (2006.01)
*G01T 7/00* (2006.01)
*H01J 35/02* (2006.01)

(56) References Cited

OTHER PUBLICATIONS

Weidenspointner, et al., "Strategy for calibrating the non-linear gain of the DSSC detector for the European XFEL", Nuclear Science Symposium and Medical Imaging Conference, Oct. 23, 2011.
Karafasoulis, et al., "Gamma spectroscopic measurements using the PID350 pixelated CdTe radiation detector", Nuclear Science Symposium Conference, Oct. 20, 2011.
Bäumer et al., "Testing an Energy-Dispersive Counting-Mode Detector With Hard X-Rays From a Synchrotron Source", IEEE Transactions on Nuclear Science, vol. 55, No. 3, June 2008.

* cited by examiner

X-RAY DETECTOR, IMAGING APPARATUS AND CALIBRATION METHOD

CROSS REFERENCE TO RELATED APPLICATIONS

This application is the U.S. National Phase application under 35 U.S.C. § 371 of International Application No. PCT/EP2015/079175, filed Dec. 9, 2015, published as WO 2016/091981 on Jun. 16, 2016, which claims the benefit of European Patent Application Number 14197459.2 filed Dec. 11, 2014. These applications are hereby incorporated by reference herein.

FIELD OF THE INVENTION

The present invention relates to an x-ray detector, an x-ray detection apparatus, an imaging apparatus and a calibration method for calibrating an x-ray detector.

BACKGROUND OF THE INVENTION

Energy calibration in semiconductor detectors (also called photon counting detectors, as e.g. known from WO 2014/087290 A1) is conventionally performed by use of gamma ray sources of known energy or by use of K-edge filters.

In the method using gamma ray sources the pixel array is irradiated with a mono-chromatic gamma ray source of known energy. The irradiation needs not be homogenous on the entire pixel array. During the irradiation a so-called threshold scan or threshold sweep is performed. This measurement establishes a relationship between the most likely pulse height observed, the so-called "photo-peak" in the pulse-height spectrum (PHS) (typically measured in DAC (digital-to-analog-conversion) values) and the incoming energy. Gain and offset variations and position dependent incomplete charge collection all lead to measureable and significant variations in the DAC-position of the photo-peak. In order to determine gain and offset on the calibration curve between energies and DACs, a second measurement is required. This second measurement can come from a second monochromatic source with sufficiently distinct energy from the first. Under the assumption of a linear dependence between the measured DAC of the photo-peak and the incoming energy, two energy milestones are sufficient to determine offset and gain for each channel.

The method using K-edge filters is very similar. However, no gamma ray sources are needed to calibrate the energy scale. Instead, a polychromatic source spectrum can be used and the energy milestone in this case is identified with a strong change in the attenuation of a K-edge filter material. Again identified from the threshold scan under polychromatic illumination, the extracted feature allows identifying one energy milestone on the DAC scale. The same options exist for the completion of the energy calibration as in the above method, namely performing a second measurement using a different K-edge filter.

An alternative second measurement for both of the above methods makes use of the existence of a noise peak in the pulse height spectrum. The noise peak results from the counting of the electronics shot noise when the comparator is moved into the noise band at the baseline. It is an assumption that the maximal count rate observed in the absence of any radiation hitting the sensor occurs for a DAC value for which the analog signal DC coincides with the location of the threshold. This alternative is useful in combination with one of the above methods but cannot be used to perform a complete energy-calibration because it provides only one reference energy.

The problems with above two methods of energy calibration are numerous. The use of gamma ray sources is problematic due to the radiation aspect and due to continuously changing activity of the source. Besides that a very close distance needs to be maintained during the calibration measurement which is unpractical for an entire detector array like the ones used for computed tomography or even mammography. Further, this method suffers from low x-ray fluxes and, hence, long calibration times. The use of K-edge filters is more practical because x-ray tubes can be used. However, the extraction of the K-edge attenuation feature is less trivial and often leads to erroneous measurements of the energy reference. Further, polychromatic sources combined with K-edge filtration suffer from the difficult process of extracting the K-edge feature from the measured spectra, in particular for realistic spectral response functions, like observed in millimeter-sized CdTe of CZT detectors, most likely candidates for future photon counting CT scanners.

Hence, it would be desirable to have an alternative measurement option for a second energy reference in addition to the above mentioned noise peak in the pulse-height spectrum (PHS; i.e. the relative frequencies of measured pulse heights) to obtain the measure the gain- and/or offset-variations in those detectors.

DE 10 2010 015422 A1 discloses an x-ray detector including a directly converting semiconductor layer for converting an incident radiation into electrical signals with a band gap energy characteristic of the semiconductor layer, and at least one light source for coupling light into the semiconductor layer, wherein the generated light, for the simulation of incident x-ray quanta, has an energy above the band gap energy of the semiconductor layer. In at least one embodiment, it includes at least one evaluation unit for calculating an evaluation signal from the electrical signals generated when the light is coupled into the semiconductor layer, and at least one calibration unit for calibrating at least one pulse discriminator on the basis of the evaluation signal. This provides the prerequisites for a rapidly repeatable calibration of the x-ray detector taking account of the present polarization state without using x-ray radiation. At least one embodiment of the invention additionally relates to a calibration method for such an x-ray detector.

SUMMARY OF THE INVENTION

It is an object of the present invention to provide an x-ray detector, an x-ray detection apparatus, an imaging apparatus and a calibration method for calibrating an x-ray detector which enable an improved calibration without the above mentioned drawbacks.

In a first aspect of the present invention an x-ray detector is presented comprising:
- a directly converting semiconductor layer having a plurality of pixels for converting incident radiation into electrical measurement signals with a band gap energy characteristic of the semiconductor layer, wherein said incident radiation is x-ray radiation emitted by an x-ray source or light emitted by at least one light source, said light having an energy above the band gap energy of the semiconductor layer for the simulation of incident x-ray quanta,
- an evaluation unit for calculating evaluation signals per pixel or group of pixels from first electrical measurement signals generated per pixel or group of pixels when light from said at least one light source at a first intensity is coupled into the semiconductor layer and second electrical measurement signals generated per pixel or group of pixels when light from said at least one light source at a second intensity is coupled into the semiconductor layer, wherein said evaluation unit is configured to detect per pixel or group of pixels a noise peak in said first and second electrical measurement signals and to determine offset and gain per pixel or group of pixels from the detected noise peaks, a detection unit for determining detection signals from electrical measurement signals generated when x-ray radiation is incident onto the semiconductor layer, and a calibration unit for calibrating the detection unit on the basis of the evaluation signals.

In a further aspect of the present invention a detection apparatus is presented comprising:

an x-ray detector as disclosed herein and at least one light source for coupling light into the semiconductor layer, wherein the generated light, for the simulation of incident x-ray quanta, has an energy above the band gap energy of the semiconductor layer.

In a further aspect of the present invention an imaging apparatus is presented comprising:

a radiation source for emitting radiation through an imaging area, an x-ray detector as disclosed herein for detecting radiation from said imaging area, a gantry to which at least said x-ray detector is mounted and which allows rotation of said x-ray detector around said imaging area, and a controller for controlling said x-ray detector to detect radiation at a plurality of projection positions during rotation around said imaging area.

In still another aspect of the present invention a calibration method is presented for calibrating an x-ray detector comprising a directly converting semiconductor layer having a plurality of pixels for converting incident radiation into electrical measurement signals with a band gap energy characteristic of the semiconductor layer and at least one light source for coupling light into the semiconductor layer, wherein the generated light, for the simulation of incident x-ray quanta, has an energy above the band gap energy of the semiconductor layer, said method comprising:

acquiring first electrical measurement signals generated per pixel or group of pixels when light from said at least one light source at a first intensity is coupled into the semiconductor layer, acquiring second electrical measurement signals generated per pixel or group of pixels when light from said at least one light source at a second intensity is coupled into the semiconductor layer, calculating evaluation signals per pixel or group of pixels from the acquired first electrical measurement signals and the acquired second electrical measurement signals by detecting per pixel or group of pixels a noise peak in said first and second electrical measurement signals and determining offset and gain per pixel or group of pixels from the detected noise peaks, determining detection signals from electrical measurement signals generated when x-ray radiation is incident onto the semiconductor layer, and calibrating the x-ray detector on the basis of the evaluation signals.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, imaging apparatus, computer program and medium have similar and/or identical preferred embodiments as the claimed detector and the claimed detection apparatus and as defined in the dependent claims.

The x-ray detection principle in semiconductor x-ray detectors is via the generation of electron-hole pairs. After their generation, these are subject to a strong electric field generated by a high voltage between the metallic cathode and the anodes on the sensor. This is very similar to the functional principle used in photo-conductors and photo-diodes in the optical domain. Most importantly, signal generation is subject to exactly the same conditions in both cases. An electrical signal can only be generated when the energy of the incoming radiation is larger than the band-gap of the semiconductor, which for CZT or CdTe (which materials are often used in the semiconductor layer) this is about 1.5 eV.

If the above condition is fulfilled, the photon energy is sufficient to excite one electron from the top of the valence band to the bottom of the conduction band. This corresponds to the generation of an electron-hole pair. The mobility of both the electron and the hole contribute to the conductivity of the sensor which by mere thermal excitation would be orders of magnitude smaller. Generally, the above condition is fulfilled for the entire visible range of the electromagnetic spectrum including portions of the near infrared. 1.5 eV corresponds to about 830 nm of wavelength.

The irradiation of the semiconductor layer with light generates a photo-current in the semiconductor layer, similar to the photo-current in a conventional photo-diode. According to the present invention light in the calibration mode (in which no x-ray radiation is emitted by the x-ray source of the imaging device) at two different intensity levels is subsequently coupled into the semiconductor layer, i.e. two electrical measurement signals are generated at the two different light intensities. It should be noted that one of the light intensities at which one of the electrical measurement signal is generated may also be zero, i.e. no light is coupled into the semiconductor layer, whereas for generation of the second electrical measurement signal light at a certain (e.g. predetermined) light intensity is coupled into the semiconductor layer. Hereby, it shall be noted that the irradiation of the semiconductor layer with light at two different intensities can be obtained either by continuous light, whereby the light intensity is switched, or by pulsed light, whereby e.g. the pulse height, pulse width and/or pulse rate of the light pulses may be changed.

This photo-current obtained by continuous light irradiation of the detector generates a DC signal which shifts the baseline for the analog signal in the detection unit (which is often configured as ASIC), which is generally DC coupled to the semiconductor layer. This baseline shift (obtained by changing the light intensity between the generation of the first and second electrical measurement signals) can be detected by a shift of the noise peak, i.e. the present invention is based on the idea to detect per pixel or group of pixels a noise peak in first and second electrical measurement signals. The absolute amount of shift of the noise peak will depend on the global light intensity but also, most importantly, on the pixel dependent (local) gain of the readout channel. By measuring the baseline shift at the two light intensity levels (e.g. with and without light), gain and offset for all channels (i.e. per pixel or group of pixels) can be found.

In this context DC coupling may be achieved by coupling of a resistor at the input of the amplifier and not a capacitance. In case the input is coupled via a capacitance there is no DC component that is transmitted (obviously) and the detector becomes AC coupled. For AC coupling there is no DC component and the idea of the present invention cannot be used by using continuous light illumination. But the calibration by light pulsing with different intensities or different light pulse durations would still be possible.

It shall be noted that the proposed energy calibration is not limited to the determination of offset and gain. Generally, two measurements are made to obtain offset and gain assuming that the relationship between input and output is linear. However, sometimes the x-ray detector shows non-linearities which could be taken into account by measuring at three or more different light intensities (e.g. once without light and twice at different light intensities or three times at three different light intensities). For instance, for energy calibration 2nd order terms may be obtained characterizing potential non-linearities of the detector. The 2nd order term may be obtained by assuming the following relationship between DAC value and energy E: DAC=a0+a1 E+a2E$^2$ with a0 being the offset, a1 being the gain and a2 being the next to linear coefficient, that could be determined by measuring the DAC of a third intensity level. Hence, in an embodiment said evaluation unit is configured to calculate evaluation signals per pixel or group of pixels from at least three electrical measurement signals generated per pixel or group of pixels when light from said at least one light source at three different intensities is coupled into the semiconductor layer.

According to an embodiment said evaluation unit is configured to perform a threshold scan to obtain said first and second electrical measurement signals. Such a threshold scan and how to perform it is generally known, e.g. from Christian Bäumer et al., "Testing an Energy-Dispersive Counting-Mode Detector With Hard X-Rays From a Synchrotron Source", IEEE TRANSACTIONS ON NUCLEAR SCIENCE, VOL. 55, NO. 3, JUNE 2008. This provides a rather easy but reliable way to obtain said first and second electrical measurement signals.

In further embodiments said evaluation unit is configured to determine the offset per pixel or group of pixels from the absolute threshold value of the noise peak in a threshold scan performed to obtain said first electrical measurement signals and/or to determine the gain per pixel or group of pixels from absolute difference in the threshold values of the noise peak in a first threshold scan performed to obtain said first electrical measurement signals and a second threshold scan performed to obtain said second electrical measurement signals and from the intensity level of the light coupled into the semiconductor layer during the generation of the first and second electrical measurement signals.

Preferably, the x-ray detection apparatus comprises a single light source for coupling light into the semiconductor layer. In other embodiments the x-ray detection apparatus comprises a plurality of light sources, in particular a single light source per pixel or group of pixels, for coupling light into the semiconductor layer. The number of light sources generally depends on the current design and any mechanical constraints, particularly with respect to the arrangement of the light source(s). Using two different sources avoids the need to switch intensities. Alternatively, source 1 can be used for E1, source 2 for E2, sources 1+2 for E3=E1+E2, i.e. no source for the noise peak.

In another embodiment beam widening optics and/or beam guiding optics are provided for beam widening and/or beam guiding of the light emitted from said at least one light source onto the semiconductor layer. Such optics may include one or more lenses, prisms, (e.g. removable or displaceable) mirrors, telescope optics, optical fibers, diffraction gratings, etc. Such means allow the arrangement of the one or more light sources at an appropriate position with respect to the semiconductor layer, e.g. at a position at a side, i.e. outside of the (direct) path of the x-ray radiation beam, as proposed in another embodiment, so that the light is guided by appropriate optics to the semiconductor layer. This takes into account the collimation system often found in x-ray systems.

A diffraction grating may e.g. be provided for diffracting the light onto the pixels of the semiconductor layer. This is particularly useful in case of using a single light source so that each pixel can be illuminated with light as homogeneously and as equal as possible in an efficient way.

Generally, short light (e.g. laser light) pulses can be used to generate a certain amount of charge in a pixel and hence also addressing the case of AC coupling of the sensor to the ASIC. The wide range of available laser powers, frequencies, pulse durations and repetition frequencies makes the laser a useful tool to tune the amount of charge generated in each pixel very precisely, reproducibly and periodically. This makes a laser an advantageous option. If the laser pulses and the noise peak references are used to perform the energy calibration, generally there remains no need for any x-ray based calibration during the entire lifetime of the detector.

With the pulsing of the light, e.g. at different pulse lengths, first and second electrical measurement signals can be generated that are useful for energy calibration. Contrary to continuous light illumination, the noise peak will not be shifted but the light pulses themselves will generate signal pulses much like the x-ray photons if only they are intense enough. This could also be used as a calibration with a gamma ray source.

Alternatively, however, a continuous light illumination of the semiconductor layer may be used avoiding the need for controlling the pulsed emission of light. Hence, said at least one light source of the x-ray detection apparatus may be configured for pulsed or continuous emission of light.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
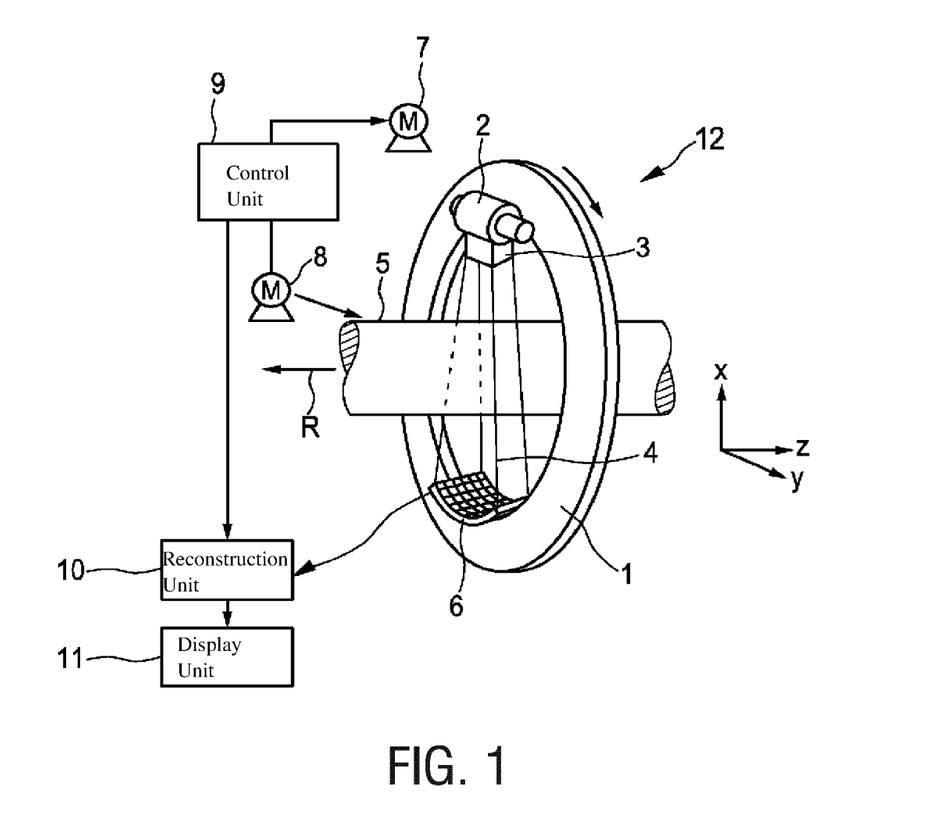
FIG. 1 shows a schematic diagram of an embodiment of an imaging system according to the present invention.

FIG. 1 shows schematically and exemplarily an imaging apparatus 12 according to the present invention for imaging an object, in this example being a computed tomography (CT) apparatus. The CT apparatus 12 includes a gantry 1, which is capable of rotation about a rotational axis R, which extends parallel to a z direction. A radiation source 2 (also called photon source), which may be a polychromatic x-ray tube, is mounted on the gantry 1. The radiation source 2 is provided with a collimator 3, which forms a (e.g. conical) radiation beam 4 from the radiation (photons) generated by the radiation source 2. The radiation traverses an object of examination, such as a patient, arranged in an (e.g. cylindrical) imaging area 5 (also called examination zone). After having traversed the imaging area 5, the radiation beam 4 is incident on an x-ray detector 6, which comprises a two-dimensional detection surface. The detector 6 is also mounted on the gantry 1.

The CT apparatus 12 comprises two motors 7, 8. The gantry 1 is driven at a preferably constant but adjustable angular speed by the motor 7. The motor 8 is provided for displacing the object, for example, a patient, who is arranged on a patient table in the imaging area 5, parallel to the direction of the rotational axis R or the z axis. These motors 7, 8 are controlled by a control unit 9, for instance, such that the radiation source 2, the detector 6 and the imaging area 5 move relative to each other along a helical directory. However, it is also possible that the object is not moved, but that only the radiation source 2 and the detector 6 are rotated, i.e. that the radiation source 2 moves along a circular trajectory relative to the object or the imaging area 5. Furthermore, in another embodiment, the collimator 3 can be adapted for forming another beam shape, in particular a fan beam, and the detector 6 can comprise a detection surface, which is shaped corresponding to the other beam shape, in particular to the fan beam.

During a relative movement of the radiation source 2 and the imaging area 5, the detector 6 generates detection values (also called detection signals; preferably one detection value per pixel, i.e. per detection element of a preferably two-dimensional array of detection elements) depending on the radiation incident on the detection surface of the detector 6. The detection values are preferably provided to a reconstruction unit 10 for reconstructing an image of the object based on the detection values. The image reconstructed by the reconstruction unit 10 may be provided to a display unit 11 for displaying the reconstructed image. The control unit 9 is preferentially also adapted to control the radiation source 2, the detector 6 and the reconstruction unit 10.

Figure 2:
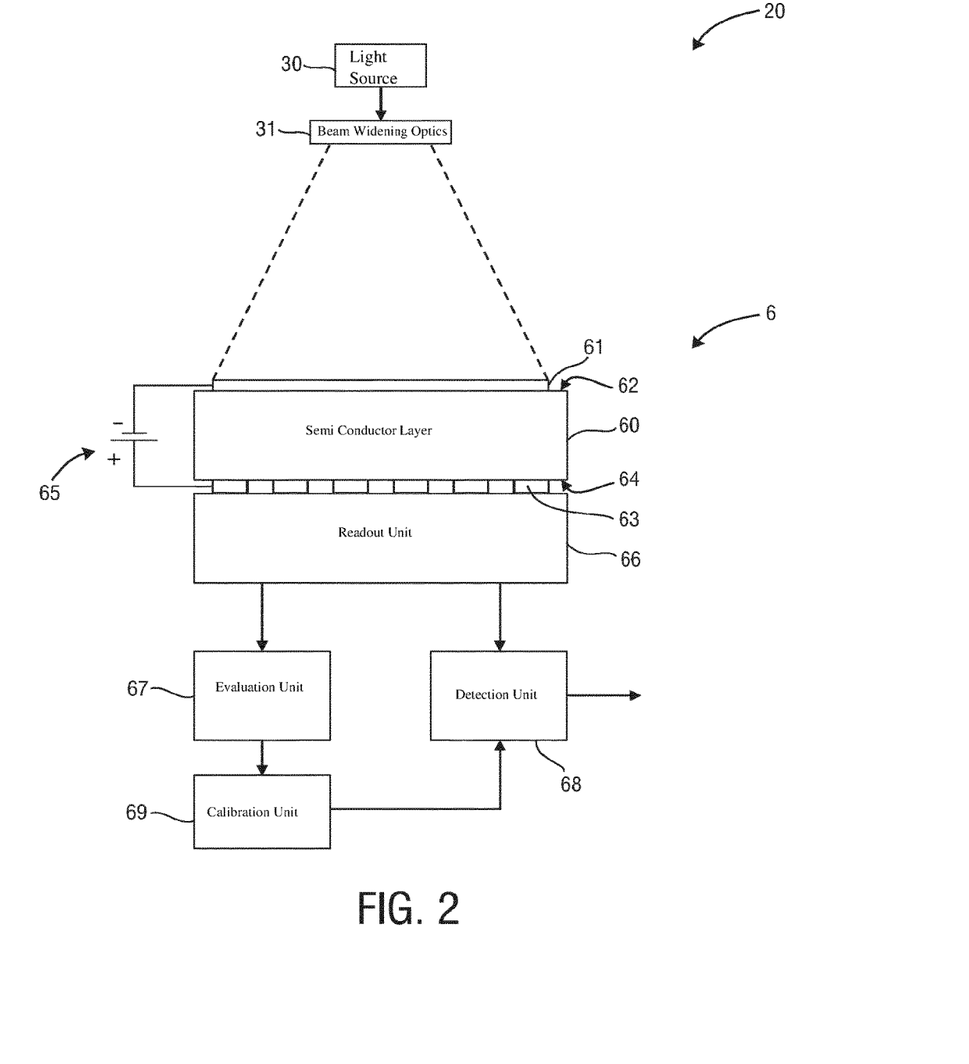
FIG. 2 shows a schematic diagram of a first embodiment of an x-ray detection apparatus including an x-ray detector according to the present invention.

According to the present invention an improved calibration of the x-ray detector 6 is possible. A corresponding embodiment of an x-ray apparatus 20 including an embodiment of an x-ray detector 6 and at least one light source 30 is shown in FIG. 2. By use of this embodiment the calibration mode as performed according to the present invention shall be explained. The x-ray source 2 and other elements of the imaging apparatus are not shown in this figure.

The x-ray detector 6 comprises a directly converting (photon counting) semiconductor layer 60 having a plurality of pixels for generating electron-hole pairs and thus for converting incident radiation into electrical measurement signals with a band gap energy characteristic of the semiconductor layer 60. The semiconductor layer 60 carries a cathode electrode 61 arranged on a first side 62 of said semiconductor layer facing incident radiation 4 and a pixelated anode electrode 63 arranged on a second side 64 of said semiconductor element 60 opposite said first side 62. The x-ray detector 6 further comprises a power source 65 for applying a bias (DC) voltage between said cathode electrode 61 and said anode electrode 63. Still further, a readout unit 66 is provided for reading out electrical signals from said pixelated anode electrode 63.

In operation mode, in which detection signals shall be acquired for generating images, the incident radiation is x-ray radiation emitted by the x-ray source 2. In calibration mode, which is activated before installing the imaging system and later on from time to time, e.g. once per day, once per week, once per month, the incident radiation is light emitted by the at least one light source 30, whereby said light has an energy above the band gap energy of the semiconductor layer 60 for the simulation of incident x-ray quanta.

The x-ray detector 6 further comprises an evaluation unit 67 for calculating evaluation signals per pixel or group of pixels (e.g. for each pixel) from first electrical measurement signals generated per pixel or group of pixels when light from said at least one light source 30 at a first intensity (which may also be zero) is coupled into the semiconductor layer 60 and second electrical measurement signals generated per pixel or group of pixels (e.g. for each pixel) when light from said at least one light source 30 at a second intensity (different from the first intensity) is coupled into the semiconductor layer 60, whereby at both measurement stages no x-ray radiation (emitted by the x-ray source 2) is incident onto the semiconductor layer 60. Further, the evaluation unit 67 detects per pixel or group of pixels (e.g. for each pixel) a noise peak in said first and second electrical measurement signals and determines offset and gain per pixel or group of pixels (e.g. for each pixel) from the detected noise peaks.

Further, a detection unit 68 is provided for determining detection signals from electrical measurement signals generated when x-ray radiation (emitted by the x-ray source and passing through the examination area, including a person or object of examination) is incident onto the semiconductor layer 60.

Finally, a calibration unit 69 is provided for calibrating the detection unit 68 on the basis of the evaluation signals calculated by the evaluation unit 67.

The at least one light source 30 is configured for coupling light into the semiconductor layer 60, wherein the generated light, for the simulation of incident x-ray quanta, has an energy above the band gap energy of the semiconductor layer. In this embodiment the (single) light source, e.g. a laser diode with appropriate focusing means such as a lens, is arranged at the gantry 1, preferably somewhere between the x-ray source 2 and the x-ray detector 6 and preferably such that it can be moved in and out of the radiation beam 4 between the x-ray source 2 and the x-ray detector 6 so that it can be moved in for the calibration mode and moved out for the operation mode of the imaging apparatus 12.

In an embodiment a pulsed laser source is used as light source 30 that emits pulses of duration between nanoseconds and microseconds of laser light. Beam widening optics 31, also shown in FIG. 2, may optionally be provided for directing the emitted laser radiation onto the x-ray detector 6 where electron-hole pairs are generated in the semiconductor layer 60 whenever the energy of the laser photons exceeds the band gap of the material. For CZT and CdTe the band gap is about 1.5 eV, hence a wide range of laser wavelengths can be used for this purpose including the entire visible range down to the soft UV light. As an alternative to beam widening optics the element 31 may include or be configured as a diffraction grating for diffracting the light onto the pixels of the semiconductor layer.

The number of electron-hole pairs per laser pulse hitting a given detector pixel depends on the wavelength of the laser, the duration of the pulse and the intensity, in short the total energy contained within one pulse and can easily be controlled in a very convenient manner. By modulating the pulse duration, the energy per pulse can be switched quasi-continuously and several energy milestones can be realized from one single device. A single reference however is already sufficient when combined with the noise peak feature in the PHS. Essentially the DAC of the noise peak, measured without x-rays, already provides the offset a0 in the formula shown above in the introduction. The energy per laser pulse hitting one sensor (i.e. one pixel) to provide an energy reference should be chosen in such a way that a large part of the range of the DAC (digital-to-analog converter) is covered by the noise peak and the second laser induced photo peak in associated threshold scans. The DAC is primarily part of the detection unit 68. It is used to set a threshold from a digital value corresponding to a certain energy (pulse-height) value.

When an x-ray detector is calibrated in the above manner, the calibration for the detection of x-rays remains incomplete up to a global scaling factor for the entire x-ray detector. This is because even though all pixels can be subject to exactly the same laser pulses and hence the same number of electron-hole pairs can be produced in each of them, the differences in conversion efficiencies between x-ray radiation and laser light do not allow a direct reference of the DAC scale in terms of measured x-ray energies.

This global scale factor however is independent of the individual pixel responses to laser light or x-ray radiation and can be determined once, e.g. prior to shipment and installation of the x-ray detector, and likely needs not to be determined again during the lifetime of the detector. Three feasible options for the determination of the global gain conversion factor would be the onetime use of a K-edge filter, a monochromatic source or a simple sensing of the maximum recorded pulse height given by kVp at the high voltage generator. All three means allow the determination of the response of the detector to x-rays as compared to optical light. The K-edge filter method introduces a K-edge attenuator into the beam and a threshold scan is performed to extract the location of the K-edge energy, hence providing an independent known energy milestone. Secondly, the use of a monochromatic source and subsequent measurement of the location of the photo-peak allows the extraction of the known DAC value and, thirdly, a threshold scan performed around the DAC values close to the kVp energy of the tube voltage setting allow to extract the energy milestone corresponding to the energy of the highest possible energy in the x-ray spectrum.

Figure 3:
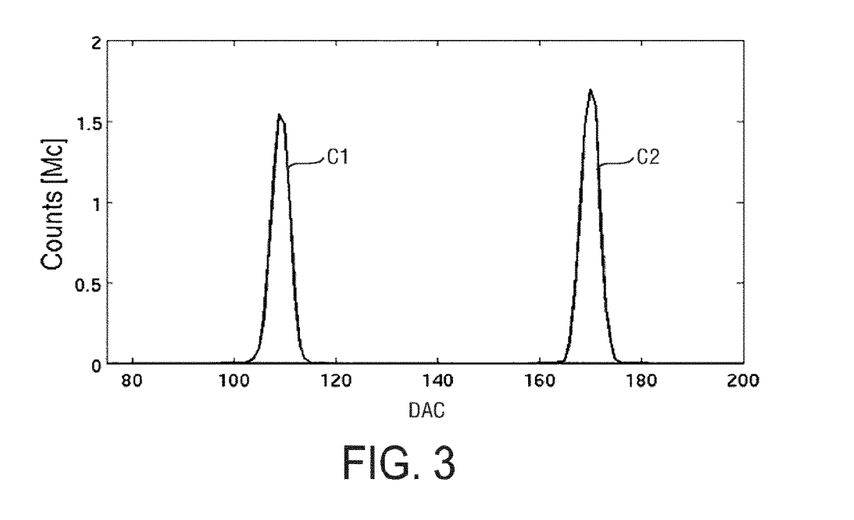
FIG. 3 shows a diagram illustrating the baseline shift of the noise peak as in a threshold scan.

FIG. 3 shows a diagram illustrating the results of a threshold scan of an embodiment of an x-ray detector according to the present invention having a CZT crystal as semiconductor layer 60. During a threshold scan the illumination conditions are kept constant. For example, under constant x-ray illumination the pulse-height spectrum is recorded. The recording of the pulse-height spectrum is facilitated by a sequential measurements of the frequency of threshold crossing events where in the sequence the threshold values are scanned, i.e. incremented by small DAC steps, for example by the least significant DAC bit. Shown are in FIG. 3 the counts (Mcps, i.e. mega-counts-per-second), over the DAC values. The left curve C1 shows the noise peak without illumination, whereas the right curve C2 shows the noise peak measured under continuous illumination by the light, in this example from a common He:Ne laser at 632 nm (with 2 mW total output power). The shift in the noise peak between the two curves C1 and C2 is very pronounced and can be measured very easily. The shift in the noise peak location under illumination is a function of the gain of the ASIC channel under consideration, i.e. the channel in which the signal from one pixel is processed in the detection unit. The calibration offset is generally represented by the DAC value of the peak C1, and the calibration gain is generally represented by the difference of the DAC values of the peak C2 and the peak C1, taking into account the intensity level of the light coupled into the semiconductor layer during the generation of the first and second electrical measurement signals. Only where the peak C1 corresponds to the noise peak the C1 measurement directly reproduces the offset. The general relations are:

$$DAC_1 = a_0 + I_1 a_1$$

$$DAC_2 = a_0 + I_2 a_1$$

from which $a_0$ and $a_1$ can easily be deduced by solving the system of linear equation, similarly for three equations and three unknowns.

Figure 4A:
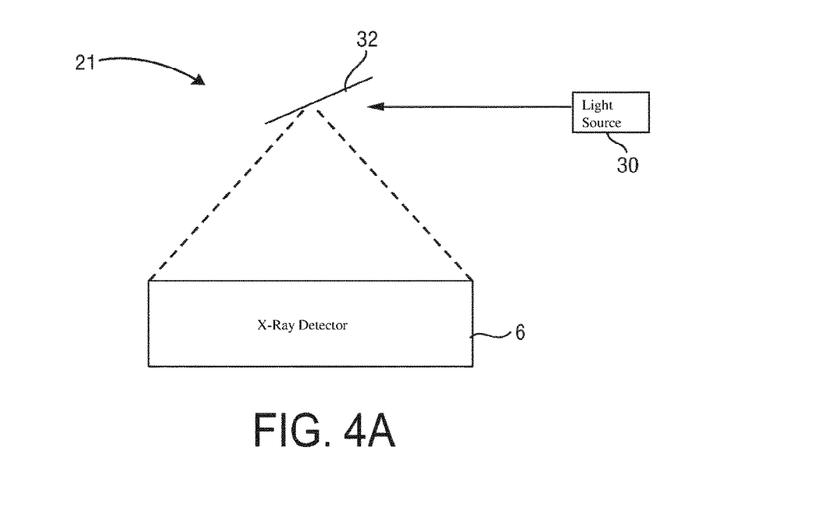
FIG. 4 shows two variations of a schematic diagram of a second embodiment of an x-ray detection apparatus according to the present invention.
Figure 4B:
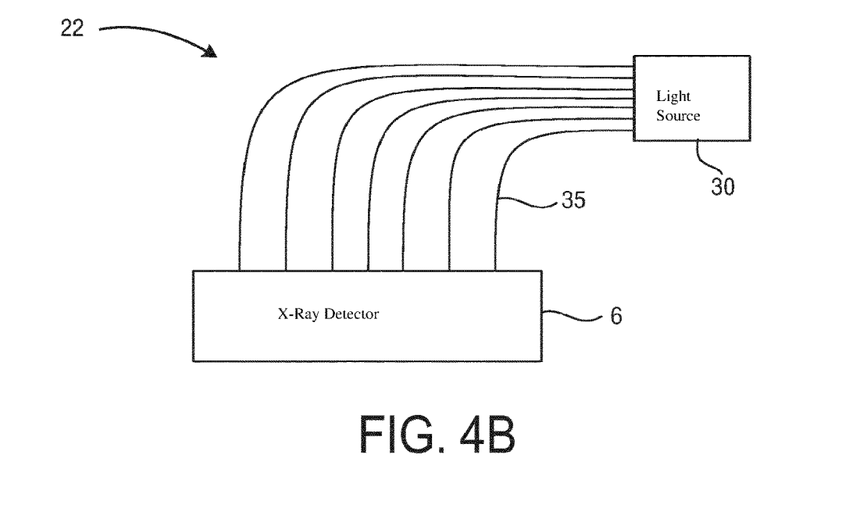

FIG. 4 shows two variations of a schematic diagram of a second embodiment of an x-ray detection apparatus 21, 22 according to the present invention. In this embodiment the light source 30 is arranged at the side of the x-ray detector 6 and not, like in the first embodiment, directly above the x-ray detector 6. In this case beam guiding optics for beam widening and/or beam guiding of the light emitted from said light source 30 onto the semiconductor layer of the x-ray detector 6. The beam guiding optics may include a removable or displaceable mirror 32 (as shown in FIG. 4A for the x-ray detection apparatus 21) or one or more optical fibers 35 (as shown in FIG. 4B for the x-ray detection apparatus 22) for light guidance, e.g. one optical fiber per pixel. The beam guiding optics may generally also be moved in and out of the radiation beam of the x-ray radiation to avoid any attenuation or other disturbance of the measurement of the x-ray radiation by the x-ray detector 6 in the operation mode. In other embodiment the beam guiding optics may be left at their position also in the operation mode.

Figure 5:
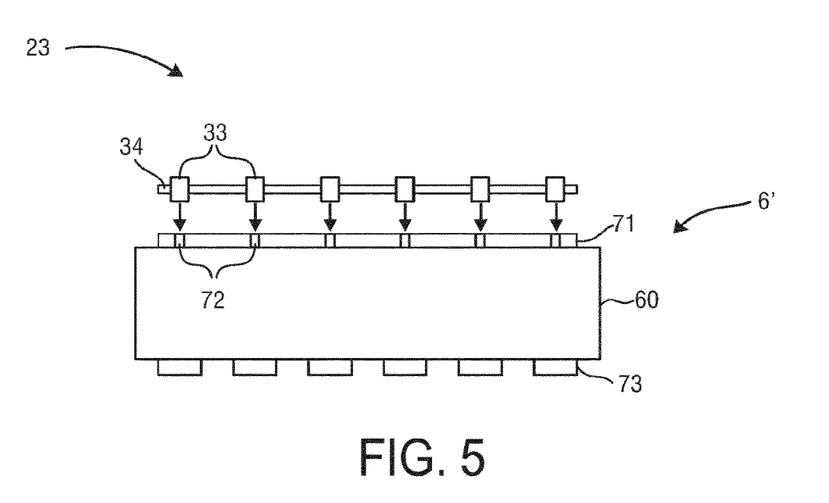
FIG. 5 shows a schematic diagram of a third embodiment of an x-ray detection apparatus according to the present invention.
Figure 6:
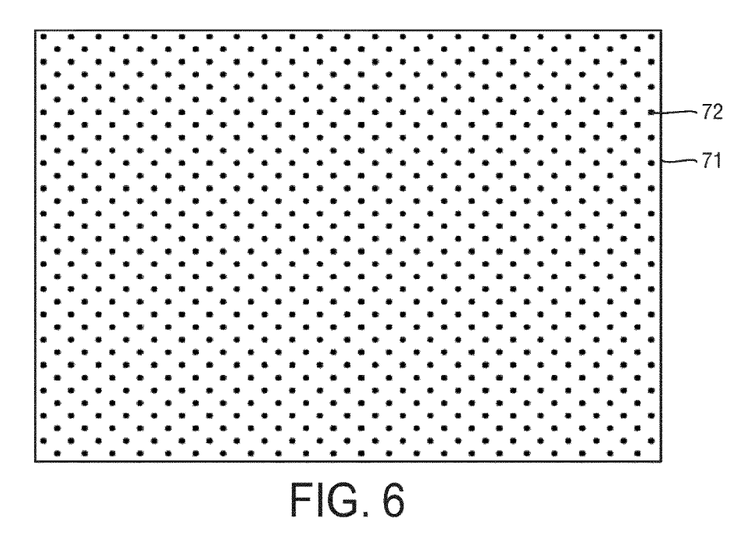
FIG. 6 shows a top view of the third embodiment of the x-ray detector.

In the second embodiment the semiconductor layer 60 is illuminated from the side. For use of the proposed energy calibration scheme in a real CT system, with the irradiation from the side, due to absorption, the intensity may not be the same for all pixels, and typically there is no space left between detector modules for irradiation. Therefore, in a third embodiment of the detection apparatus 23 shown in FIG. 5 the x-ray detector 6' is again illuminated from the top (i.e. the cathode side). In this embodiment not a single light source but a plurality of light sources 33 is used. The cathode 71 is a thin metal layer opaque for light in this embodiment. In order to transmit light, small holes 72 may be created in the thin metal layer 71 as shown in FIG. 6 depicting a top view of a detector module of the x-ray detector 6 shown in FIG. 5. The holes 72 are small in size in order not to disturb the electric field between the cathode 71 and the anode 73. There can also be multiple smaller holes per anode area. The plurality of light sources 33 are either provided within the holes 72 or at a (preferably) short distance above the holes 72, preferably one light source 33 per hole 72, and preferably include small LEDs or lasers, held by a holding layer 34. This holding layer 34 may be transparent for x-ray radiation so that it may be fixedly arranged and may be kept at its position even in the operating mode.

Preferably, the x-ray detector shall be illuminated by homogenous illumination. To achieve this various combinations of light sources and optical systems are available and may be used. For instance, an LED array or lasers with a micro-lens array or a light pipe homogenizing rods (or, generally, a light homogenizer) utilizing total internal reflection to turn a non-uniform light source into uniform illumination may be used. To eliminate remaining imperfections of homogeneity the homogeneous light source can be rotated during illumination.

It should be noted that only relative gain values are generally computed by this method. One absolute gain conversion factor from x-rays to optical input may be obtained in a separate measurement, e.g., via a gamma-ray measurement for one pixel or a single measurement where the feature in the detected spectrum is taken to be the kVp setting of the x-ray tube setting the maximal energy to be expected in the x-ray spectrum. Some ASICs feature an active leakage current compensation (baseline restoration). This compensation is preferably disabled since otherwise the restoration circuit will compensate for the photo-current generated by the incident light. The gain calibration should not be effected by the state of the BLR (baseline restauration). The data for the gain calibration can be acquired without BLR even though it is utilized during measurements.

Figure 7:
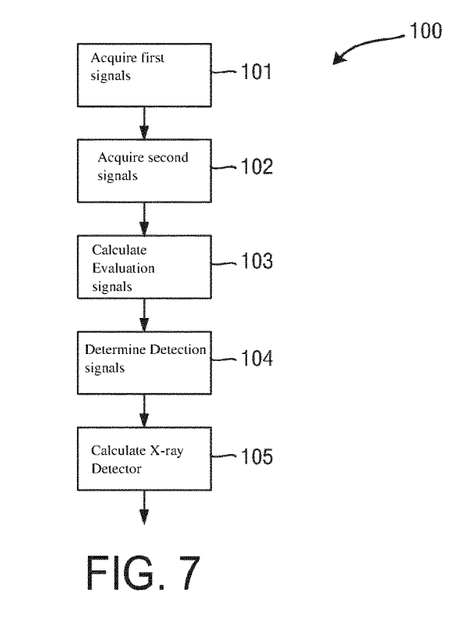
FIG. 7 shows a flow chart of a method according to the present invention.

FIG. 7 shows a flow chart of a calibration method 100 for calibrating an x-ray detector according to the present invention. In a first step 101 first electrical measurement signals generated per pixel or group of pixels when neither light from said at least one light source nor x-ray radiation is incident onto the semiconductor layer are acquired. In a second step 102 second electrical measurement signals generated per pixel or group of pixels when light from said at least one light source is coupled into the semiconductor layer are acquired. In a third step 103 evaluation signals are calculated per pixel or group of pixels from the acquired first electrical measurement signals and the acquired second electrical measurement signals by detecting per pixel or group of pixels a noise peak in said first and second electrical measurement signals and determining offset and gain per pixel or group of pixels from the detected noise peaks. In a fourth step 104, in operation mode, detection signals are determined from electrical measurement signals generated when x-ray radiation is incident onto the semiconductor layer. In a fifth step 105 the x-ray detector is calculated on the basis of the evaluation signals.

The invention is generally applicable to all energy-sensitive detectors requiring regular energy calibration, like those used in computed tomography, i.e., spectral CT, spectral x-ray imaging and photon counting mammography.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. An X-ray detector comprising:
a directly converting semiconductor layer having a plurality of pixels for converting incident radiation into electrical measurement signals with a band gap energy characteristic of the semiconductor layer, wherein said incident radiation is x-ray radiation emitted by an x-ray source or light emitted by at least one light source, said light having an energy above the band gap energy of the semiconductor layer for simulation of incident x-ray quanta,
an evaluation unit for calculating evaluation signals per pixel or group of pixels from first electrical measurement signals generated per pixel or group of pixels when light from said at least one light source at a first intensity is coupled into the semiconductor layer and second electrical measurement signals generated per pixel or group of pixels when light from said at least one light source at a second intensity is coupled into the semiconductor layer, wherein said evaluation unit is configured to detect per pixel or group of pixels a noise peak in said first and second electrical measurement signals and to determine offset and gain per pixel or group of pixels from the detected noise peaks,
a detection unit for determining detection signals from electrical measurement signals generated when x-ray radiation is incident onto the semiconductor layer, and
a calibration unit for calibrating the detection unit on the basis of the evaluation signals.

2. The X-ray detector as claimed in claim 1, wherein said evaluation unit is configured to perform a threshold scan to obtain said first and second electrical measurement signals.

3. The X-ray detector as claimed in claim 2, wherein said evaluation unit is configured to determine the offset per pixel or group of pixels from an absolute threshold value of the noise peak in a threshold scan performed to obtain said first electrical measurement signals.

4. The X-ray detector as claimed in claim 2, wherein said evaluation unit is configured to determine the gain per pixel or group of pixels from an absolute difference in threshold values of the noise peak in a first threshold scan performed to obtain said first electrical measurement signals and a second threshold scan performed to obtain said second electrical measurement signals and from the intensity level of the light coupled into the semiconductor layer during the generation of the first and second electrical measurement signals.

5. The X-ray detector as claimed in claim 1, wherein said evaluation unit is configured to calculate evaluation signals per pixel or group of pixels from at least three electrical measurement signals generated per pixel or group of pixels when light from said at least one light source at three different intensities is coupled into the semiconductor layer.

6. The X-ray detection apparatus comprising:
an x-ray detector as claimed in claim 1 and
at least one light source for coupling light into the semiconductor layer, wherein the generated light, for the simulation of incident x-ray quanta, has an energy above the band gap energy of the semiconductor layer.

7. The X-ray detection apparatus as claimed in claim 6, comprising a single light source for coupling light into the semiconductor layer.

8. The X-ray detection apparatus as claimed in claim 6, comprising a plurality of light sources, including a single light source per pixel or group of pixels, for coupling light into the semiconductor layer.

9. The X-ray detection apparatus as claimed in claim 6, further comprising at least one of beam widening optics for beam widening of the light emitted from said at least one light source onto the semiconductor layer or beam guiding optics for beam guiding of the light emitted from said at least one light source onto the semiconductor layer.

10. The X-ray detection apparatus as claimed in claim 9, comprising one or more removable or displaceable mirrors, fiber optics, diffraction gratings for diffracting the light onto the pixels of the semiconductor layer and/or lenses.

11. The X-ray detection apparatus as claimed in claim 6, wherein said at least one light source is arranged outside of the path of the x-ray radiation.

12. The X-ray detection apparatus as claimed in claim 6, wherein said at least one light source is configured for pulsed or continuous emission of light.

13. An imaging apparatus comprising:
a radiation source for emitting radiation through an imaging area,
an x-ray detection apparatus as claimed in claim 6 for detecting radiation from said imaging area,
a gantry to which at least said x-ray detector is mounted and which allows rotation of said x-ray detector around said imaging area, and
a controller for controlling said x-ray detection apparatus to detect radiation at a plurality of projection positions during rotation around said imaging area.

14. A calibration method for calibrating an x-ray detector comprising a directly converting semiconductor layer having a plurality of pixels for converting incident radiation into electrical measurement signals with a band gap energy characteristic of the semiconductor layer and at least one light source for coupling light into the semiconductor layer, wherein the generated light, for simulation of incident x-ray quanta, has an energy above the band gap energy of the semiconductor layer, said method comprising:
acquiring first electrical measurement signals generated per pixel or group of pixels when light from said at least one light source at a first intensity is coupled into the semiconductor layer,
acquiring second electrical measurement signals generated per pixel or group of pixels when light from said at least one light source at a second intensity is coupled into the semiconductor layer,
calculating evaluation signals per pixel or group of pixels from the acquired first electrical measurement signals and the acquired second electrical measurement signals by detecting per pixel or group of pixels a noise peak in said first and second electrical measurement signals and determining offset and gain per pixel or group of pixels from the detected noise peaks,
determining detection signals from electrical measurement signals generated when x-ray radiation is incident onto the semiconductor layer, and
calibrating the x-ray detector on the basis of the evaluation signals.

15. A non-transitory computer readable medium encoded with a computer program comprising program code for causing a computer to control an imaging apparatus to carry out the steps of the method as claimed in claim 14 when said computer program is carried out on the computer.

* * * * *